(12) United States Patent
DiGasbarro

(10) Patent No.: US 7,845,944 B2
(45) Date of Patent: Dec. 7, 2010

(54) ORAL SUCTION SWAB

(75) Inventor: Phillip Peter DiGasbarro, St. Louis, MO (US)

(73) Assignee: Trademark Medical, LLC, St. Louis, MO (US)

( * ) Notice: Subject to any disclaimer, the term of this patent is extended or adjusted under 35 U.S.C. 154(b) by 1253 days.

(21) Appl. No.: 11/416,223

(22) Filed: May 3, 2006

(65) Prior Publication Data

US 2007/0276326 A1 Nov. 29, 2007

(51) Int. Cl.
*A61C 17/06* (2006.01)
(52) U.S. Cl. ....................................... 433/91
(58) Field of Classification Search ............ 433/91, 433/93–96; 604/902, 275, 35–36
See application file for complete search history.

(56) References Cited

U.S. PATENT DOCUMENTS

| | | |
|---|---|---|
| 1,931,720 A | 10/1933 | Edgington |
| 2,180,249 A | 11/1939 | Lempert |
| 2,261,058 A | 10/1941 | Forbis |
| 2,490,168 A | 12/1949 | Strauss |
| 2,529,499 A | 11/1950 | Jankelson |
| 2,637,106 A | 5/1953 | Otis |
| 2,791,030 A | 5/1957 | Tofflemire |
| 3,018,778 A | 1/1962 | Brilliant |
| 3,090,122 A | 5/1963 | Erickson |
| 3,101,544 A | 8/1963 | Baughan |
| 3,101,545 A | 8/1963 | Baughan |
| D206,641 S | 1/1967 | Hill |
| 3,324,855 A | 6/1967 | Heimlich |
| D211,676 S | 7/1968 | Flower, Jr. |
| 3,495,917 A | 2/1970 | Truhan |
| 3,519,364 A | 7/1970 | Truhan |
| 3,520,300 A | 7/1970 | Flower, Jr. |
| 3,753,292 A | 8/1973 | Hutson |
| 3,758,950 A | 9/1973 | Krouzian |
| 3,864,831 A * | 2/1975 | Drake ................. 433/91 |
| 4,068,664 A * | 1/1978 | Sharp et al. ........... 433/91 |
| 4,158,916 A | 6/1979 | Adler |
| 4,233,025 A | 11/1980 | Larson et al. |
| 4,356,823 A | 11/1982 | Jackson |
| D269,811 S | 7/1983 | Kaufman |

(Continued)

FOREIGN PATENT DOCUMENTS

EP 447718 9/1991

*Primary Examiner*—Cris L Rodriguez
*Assistant Examiner*—Heidi M Eide
(74) *Attorney, Agent, or Firm*—Diederiks & Whitelaw, PLC

(57) ABSTRACT

A suction swab includes a suction tube having a hollow body provided with first and second open end portions and a bend portion. The hollow body includes a transverse bore arranged proximate to the second end which defines first and second openings. The resilient tip includes a main body having a first end section, a second end section and first and second opposing side sections and a central passage. The central passage extends through the main body and is open at each of the first and second end sections so as to define a first aperture arranged at the first end section and a second aperture arranged at the second end section. The resilient tip also includes a transverse passage that extends between one of the first and second opposing side sections and the central passage defining third and fourth openings which are smaller than the first and second openings.

10 Claims, 2 Drawing Sheets

U.S. PATENT DOCUMENTS

| | | |
|---|---|---|
| D270,762 S | 9/1983 | Kaufman |
| 4,429,434 A | 2/1984 | Sung-Shan |
| D274,575 S | 7/1984 | Kronner |
| 4,522,592 A | 6/1985 | Johnson |
| 4,538,631 A | 9/1985 | Prince |
| D282,698 S | 2/1986 | Newton, Jr. |
| 4,672,953 A | 6/1987 | Divito |
| 4,767,404 A * | 8/1988 | Renton .................. 433/93 |
| 4,787,599 A | 11/1988 | Nyboer |
| D306,905 S | 3/1990 | Barclay |
| 4,935,001 A | 6/1990 | George |
| D312,872 S | 12/1990 | Mahl |
| 5,071,347 A | 12/1991 | McGuire |
| 5,085,633 A | 2/1992 | Hanifl et al. |
| 5,094,616 A | 3/1992 | Levenson |
| 5,151,094 A | 9/1992 | Hanifl |
| D332,658 S | 1/1993 | Thompson |
| 5,203,699 A | 4/1993 | McGuire |
| 5,232,362 A | 8/1993 | Kanas |
| D352,998 S | 11/1994 | Hanifl |
| 5,378,226 A | 1/1995 | Hanifl et al. |
| 5,437,651 A | 8/1995 | Todd et al. |
| 5,458,563 A | 10/1995 | Stewart |
| 5,463,792 A | 11/1995 | Hogan et al. |
| 5,628,735 A | 5/1997 | Skow |
| 5,709,866 A | 1/1998 | Booras et al. |
| 5,774,925 A | 7/1998 | Pryor, III |
| 5,910,122 A | 6/1999 | D'Angelo |
| 5,921,972 A | 7/1999 | Skow |
| 5,975,897 A | 11/1999 | Propp et al. |
| 6,068,477 A | 5/2000 | Mahlmann |
| 6,074,208 A | 6/2000 | Mitchell |
| D428,137 S | 7/2000 | Phelan |
| 6,129,547 A | 10/2000 | Cise et al. |
| D435,101 S | 12/2000 | Graneto, III |
| 6,183,254 B1 | 2/2001 | Cohen |
| 6,186,782 B1 | 2/2001 | Luppi |
| 6,235,009 B1 | 5/2001 | Skow |
| 6,238,213 B1 | 5/2001 | Young et al. |
| 6,299,444 B1 | 10/2001 | Cohen |
| 6,315,556 B1 | 11/2001 | Stewart |
| D474,269 S | 5/2003 | Choksi et al. |
| 6,620,132 B1 | 9/2003 | Skow |
| 6,632,091 B1 | 10/2003 | Cise et al. |
| D483,862 S | 12/2003 | Rawlings et al. |
| D500,851 S | 1/2005 | Graneto |
| 2003/0108846 A1 | 6/2003 | Hoertsch |
| 2003/0181840 A1 | 9/2003 | Tsaur |

\* cited by examiner

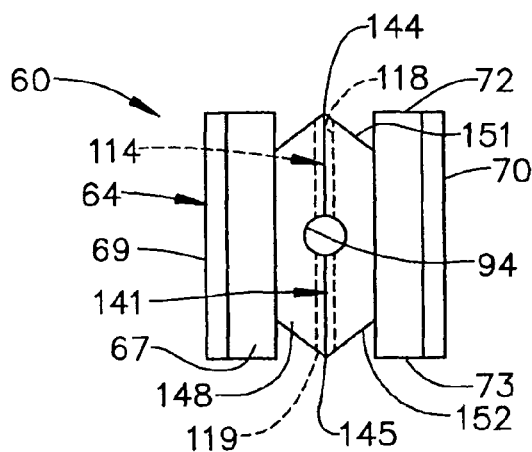
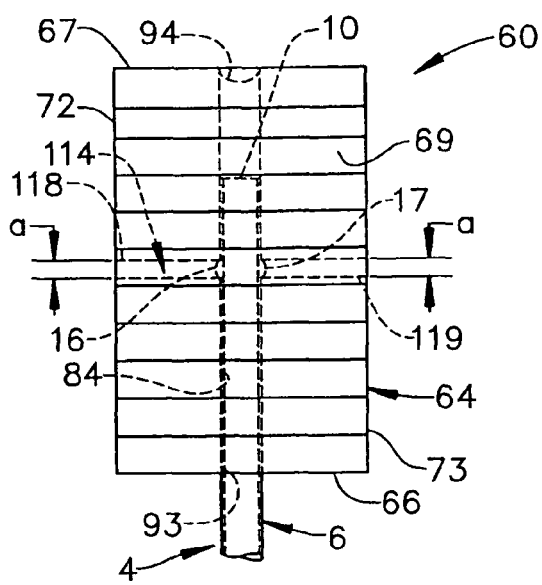
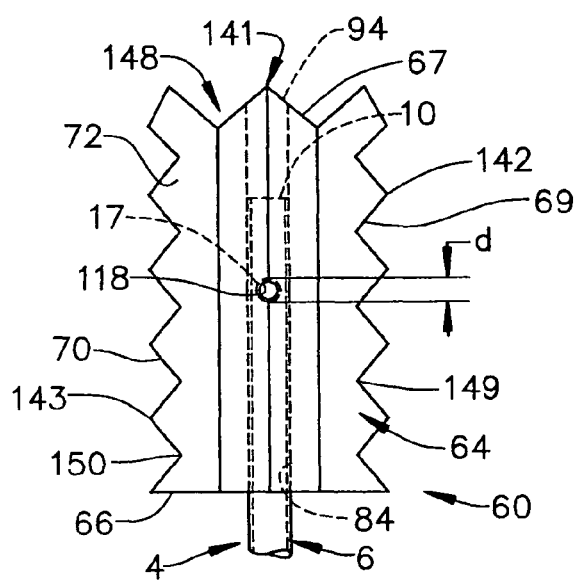
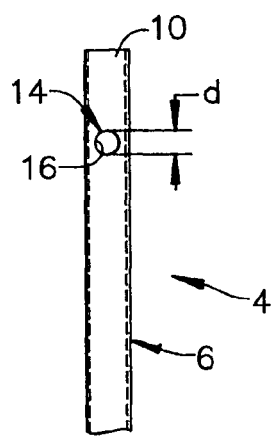
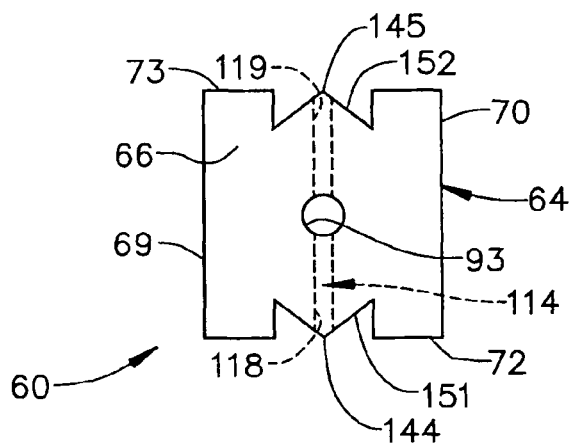

ORAL SUCTION SWAB

BACKGROUND OF THE INVENTION

1. Field of the Invention

The present invention pertains to the art of oral swabs and, more particularly, to an oral suction swab for aspirating liquid or other material from an oral cavity of a patient.

2. Discussion of the Prior Art

Suction swabs are used to perform oral care on patients who cannot swallow, such as when undergoing a dental procedure or due to some physical impairment or mechanical obstruction. Typically, the swabs are disposable and constructed in various shapes and sizes. A typical swab includes a foam head, a suction tube and a vacuum break. Often times, the foam head will include an opening in a distal end portion that leads into the suction tube to aid in aspirating fluid from an oral cavity. However, a single opening positioned in the distal end is often times not properly orientated in order to efficiently aspirate all oral fluids. In addition, if full vacuum force is applied to the swab, tissue can be undesirably drawn into the opening.

In order to address the above problems, suction swabs have been developed with a pair of aligned openings that extend through side portions of the foam head and the suction tube. The pair of openings not only allowed for better aspiration of fluids, but one of the pair of holes served as a vacuum break in the event that tissue started to extrude into another of the pair of openings. However, given the confined working space in an oral cavity, tissue can actually be extruded into both openings simultaneously. In addition, as the pair of openings were formed in the foam head and the suction tube at the same time, generally rough edges are formed in the suction tube. Any tissue drawn into a suction opening and engaging a rough edge could be bruised.

In order to allow for greater access into the oral cavity or provide a more ergonomic positioning, often times the suction tube is angled near the distal end, proximate to the foam head. The angle of the suction tube aides healthcare workers in accessing the oral cavity without requiring awkward arm positioning. However, the location of the bend is not properly positioned for all conditions, particularly for patients in intensive care units (ICU). In an ICU, a patient's head may be raised to an angle of 30 degrees or more in order to prevent a common condition referred to as ventilator associated pneumonia. If the healthcare worker employs a suction tube that is not angled or the angle of the suction tube does not correspond to the angle of the patient's head, the arm of the healthcare worker may be placed at a non-ergonomic angle which could lead to discomfort for the patient, as well as to discomfort or fatigue to the healthcare worker.

Thus, based on the above, there still exists a need for enhancements to suction swabs for aspirating oral fluids. More specifically, there exists a need for an oral suction swab having a plurality of openings that will effectively remove fluids from an oral cavity, while ensuring that tissue is not extruded into the swab. In addition, there exists a need for an oral swab having a head that is approximately angled so as to alleviate unnecessary stress, discomfort and fatigue when used in aspirating fluids from a patient.

SUMMARY OF THE INVENTION

The present invention is directed to a suction swab for aspirating fluids from an oral cavity. The suction swab includes a suction tube having an elongated hollow body provided with first and second open end portions and a bend portion, with the bend portion being preferably positioned closer to the first end portion than to the second end portion. The hollow body includes a transverse bore, arranged proximate to the second end portion, which defines first and second openings. Each of the first and second openings includes corresponding first and second diameters. The suction swab also includes a vacuum break configured to connect to a source of vacuum arranged at the first end portion, and a resilient tip arranged at the second end portion.

In accordance with the invention, the resilient tip includes a main body having a first end section, a second end section, and first and second opposing side sections. The main body includes a sculpted, outer surface and a central passage. The sculpted outer surface creates a plurality of grooves and ridges that increase an overall surface area of the resilient tip to aid in the removal of fluids from the oral cavity. In any event, the central passage extends longitudinally through the main body and is open at each of the first and second end sections so as to define a first aperture arranged at the first end section and a second aperture arranged at the second end section. The first aperture receives the second end portion of the suction tube, while the second aperture is exposed so as to provide a passage for aspirated fluids into the elongated hollow body.

In further accordance with the invention, the resilient tip also includes a transverse passage that extends between one of the first and second opposing side sections and through the central passage so as to define third and fourth openings. The third and fourth openings align with the first and second openings formed in the suction tube to provide additional passages for the aspirated fluid. The third and fourth openings include corresponding third and fourth diameters which are smaller than the first and second diameters. With this advantageous arrangement, in the event oral tissue is extruded into the suction swab, portions of the resilient tip are also drawn into the first and second openings to prevent the tissue from being damaged. In any event, the present invention provides a versatile device for aspirating fluids from an oral cavity. Application of a vacuum force at the first end of the suction tube results in associated vacuum forces at each of the second aperture and the third and fourth openings in order to provide a multi-sided device for aspirating fluid from an oral cavity.

Additional objects, features and advantages of the present invention will become more readily apparent from the following detailed description of a preferred embodiment when taken in conjunction with the drawings wherein like reference numerals refer to corresponding parts in the several views.

BRIEF DESCRIPTION OF THE DRAWINGS

FIG. 2 is a top view of a resilient tip portion of the oral swab of FIG. 1;

FIG. 3 is a left side view of the resilient tip of FIG. 2, with the right side view preferably being a mirror image;

FIG. 4 is a bottom view of the resilient tip of FIG. 2;

FIG. 5 is another side view of the resilient tip of FIG. 2, with an opposing side view preferably being a mirror image; and FIG. 6 is a partial side view of a suction tube portion of the suction swab of FIG. 1.

DETAILED DESCRIPTION OF THE PREFERRED EMBODIMENT

Figure 1:
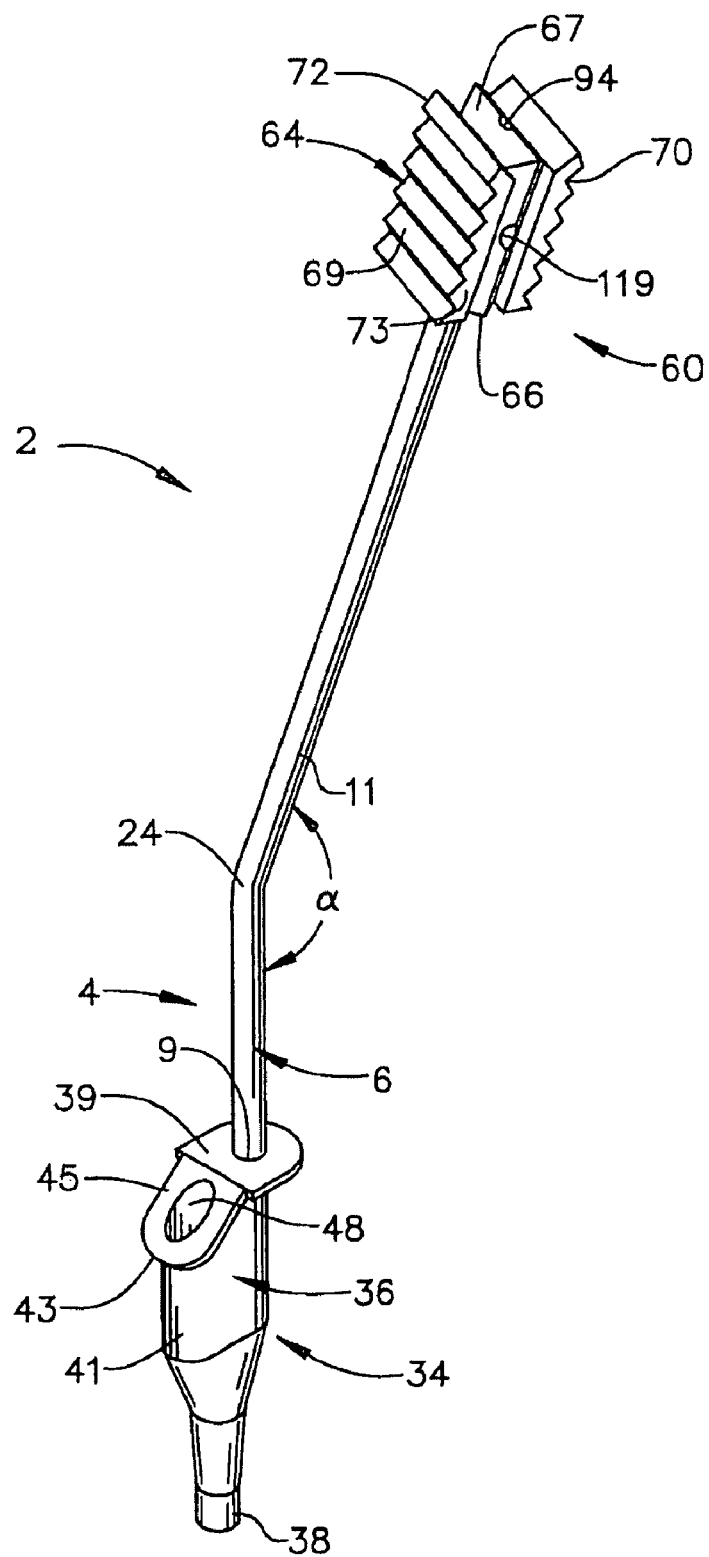
FIG. 1 is a perspective view of an oral suction swab constructed in accordance with the present invention.

With initial reference to FIGS. 1 and 6, a suction swab constructed in accordance with the present invention is generally indicated at 2. Suction swab 2 includes a suction tube 4 having an elongated hollow main body 6 provided with first and second end portions 9 and 10 spaced by an intermediate portion 11. Suction tube 4 includes a transverse bore 14 arranged proximate to second end portion 10. Transverse bore 14 defines a first opening 16 having a first diameter (d) that opens or leads into hollow main body 6, and a second opening 17 (see FIGS. 3 and 5) having a second diameter (d) which also leads into hollow main body 6. Suction tube 4 is shown to include a bend portion 24 having an angle (α) which, in accordance with the most preferred form of the invention, is approximately 30°. As will be discussed further below, in accordance with one embodiment of the invention, bend portion 24 is positioned closer to first end portion 9 than to second end portion 10, especially when main body 6 is in the order of 6-8 inches (approximately 15.25-20.3 cm) in overall length. In a preferred form, the respective lengths have 1:1.25 or greater ratio.

Suction tube 4 is also shown in FIG. 1 to include a vacuum break 34 having a main body 36 provided with a first end 38 which leads to a second end 39 through an intermediate or handle member 41. First end 38 is adapted to be placed in fluid communication with a source of vacuum (not shown) and second end 39 is joined to suction tube 4. Handle member 41 is provided with a switch member 43 including an angular surface 45 having formed therein an orifice 48. Orifice 48 is in fluid communication with first end 38 and within suction tube 4 at second end 39. With this construction, a vacuum force applied at first end 38 will draw air through orifice 48 rather than through suction tube 4. However, covering orifice 48 will cause the vacuum force to be drawn through suction tube 4 in a manner that will be discussed more fully below.

Referring to FIGS. 1-5, suction swab 2 includes a resilient tip 60 having a main body 64 including a first end section 66, a second end section 67, first opposing side sections 69, 70 and second opposing side sections 72, 73. Resilient tip 60 also includes a central, longitudinal passage 84 that traverses first and second end sections 66 and 67 so as to define an elongated bore traversing between a first aperture 93 arranged at first end section 66 and a second aperture 94 arranged at second end section 67. In accordance with the invention, first aperture 93 receives second end portion 10 of suction tube 6 as shown in FIGS. 3 and 5.

In further accordance with the invention, resilient tip 60 includes a transverse passage 114 that, in accordance with the embodiment shown, extends between second opposing side sections 72 and 73 and connects with passage 84. Transverse passage 114 defines third and fourth openings 118 and 119, each having respective third and fourth diameters (a). In further accordance with the most preferred form of the invention, third and fourth diameters (a) of third and fourth openings 118 and 119 are smaller than first and second diameters (d) of first and second openings 16 and 17. With this construction, in the event that oral tissue is extruded into third and/or fourth openings 118, 119, portions of main body 64 of resilient tip 60 will also be drawn into corresponding ones of openings 16 or 17 to cover any sharp edges which may exist, thereby preventing any damage to the tissue.

Finally, each side section 67, 69, 70, 72 and 73 includes a plurality of sculpted surfaces that define, for example, peaks 141-145 and grooves 148-152 respectively. Peaks 141-145 and grooves 148-152 increase an overall surface area of resilient tip 60 so as to result in a corresponding increase in absorbency. That is, the particular shape, number and configuration of peaks 141-145 and grooves 148-152 enhance cleaning of the oral cavity by providing roughened and angled surfaces which improve abrasion qualities.

At this point, it should be readily understood that the present invention provides for an efficient means for aspirating fluids from an oral cavity. That is, by locating aperture 94 90° apart from third and fourth openings 118 and 119, suction swab 2 can be employed in various orientations in an oral cavity with a substantial reduction in the likelihood that aperture 94 and openings 118 and 119 will become simultaneously covered causing tissue to be extruded into suction swab 2. Instead, at least one of aperture 94 and openings 118 and 119 will be open to reduce tissue extrusion. Moreover, the particular location and orientation of bend portion 24 enables the effective use of suction swab 2 in aspirating fluids from patients positioned in a variety of orientations, without creating fatigue on the arm of the health case worker employing suction swab 2. Finally, the number, shape and orientation of the peaks and grooves arranged on resilient tip 60 allow suction tube 2 to be employed for a longer period without requiring replacement.

Although described with reference to a preferred embodiment of the invention, it should be readily understood that various changes and/or modifications can be made to the invention without departing from the spirit thereof. For instance, the overall number of peaks and grooves can vary without departing from the scope of the present invention. In fact, the overall shape of the tip can change from that shown and described so as to include, for example, other polygon and even cylindrical shapes. In addition, the number and shape of the aspiration holes can vary. For instance, additional and/or substitutes holes could be provided in the resilient tip which are not in alignment with the openings in the hollow tube. Furthermore, it should be recognized that a corresponding smaller aperture could be provided at the end of the resilient tip to protect oral tissue in a manner analogous to that discussed above. In general, the invention is only intended to be limited by the scope of the following claims.

I claim:

1. A suction swab device for aspirating fluids from an oral cavity comprising:
    a suction tube including:
        an elongated hollow body having first and second end portions spaced by an intermediate portion, each of the first and second end portions being open to the hollow body;
        a transverse bore arranged proximate to the second end portion, said transverse bore defining first and second openings, with the first and second openings having first and second diameters respectively; and
        a bend portion formed in the intermediate portion at a position located closer to the first end portion than to the second end portion;
    a vacuum break arranged at the first end portion, said vacuum break being adapted to be placed in fluid communication with a source of vacuum; and
    a resilient tip arranged on the second end portion of the suction tube, said resilient tip including:
        a main body having a first end section, a second end section and first and second pairs of opposing side sections;
        a central, axial passage traversing the first and second end sections so as to define a first aperture arranged at the first end section which leads through the main body to a second aperture arranged at the second end section, said first aperture receiving the second end portion of the suction tube, with the second end section of the main body projecting beyond the second end portion of the suction tube and the second aperture being in fluid communication with the hollow body; and a transverse passage extending between the first pair of opposing side sections, said transverse passage being open to the central passage and defining third and fourth openings which align with the first and second openings of the suction tube, said third and fourth openings having third and fourth diameters, with each of the third and fourth diameters being smaller than either of the first and second diameters such that, in the event that oral tissue is extruded into the third or fourth openings, portions of the resilient tip will also be drawn into corresponding ones of the first and second openings to cover any sharp edges of the suction tube which may exist and, when a source of vacuum is attached to the first end portion of the suction tube, vacuum forces are created at the second aperture and the third and fourth openings to enable the aspiration of fluid from a cavity through the elongated hollow body.

2. A suction swab device for aspirating fluids from an oral cavity comprising:

a suction tube including:

an elongated hollow body having first and second end portions spaced by an intermediate portion, each of the first and second end portions being open to the hollow body; and a transverse bore arranged proximate to the second end portion, said transverse bore defining first and second openings, with the first and second openings having first and second diameters respectively;

a vacuum break arranged at the first end portion, said vacuum break being adapted to be placed in fluid communication with a source of vacuum; and a resilient tip arranged on the second end portion of the suction tube, said resilient tip including:

a main body having a first end section, a second end section and at least one side section;

a central, axial passage traversing the first and second end sections so as to define a first aperture arranged at the first end section which leads through the main body to a second aperture arranged at the second end section, said first aperture receiving the second end portion of the suction tube, with the second end section of the main body projecting beyond the second end portion, of the suction tube and the second aperture being in fluid communication with the hollow body; and a transverse passage being open to the central passage and defining third and fourth openings which align with the first and second openings of the suction tube, said third and fourth openings having third and fourth diameters, with each of the third and fourth diameters being smaller than either of the first and second diameters such that, in the event that oral tissue is extruded into the third or fourth openings, portions of the resilient tip will also be drawn into corresponding ones of the first and second openings to cover any sharp edges of the suction tube which may exist and, when a source of vacuum is attached to the first end portion of the suction tube, vacuum forces are created at the second aperture and the third and fourth openings to enable the aspiration of fluid from a cavity through the elongated hollow body.

3. The suction swab according, to claim 2, wherein the at least one side section is provided with sculpted surfaces that define a plurality of ridges and a plurality of grooves.

4. The suction swab according to claim 2, wherein the at least one side section includes first and second pairs of opposing side sections.

5. The suction swab according to claim 4, wherein the transverse passage extends between the first pair of opposing side sections.

6. The suction swab according to claim 4, wherein each of the first and second opposing pairs of side sections is provided with sculpted surfaces that define a plurality of ridges and a plurality of grooves.

7. The suction swab according to claim 6, wherein the third and fourth openings are positioned on respective ones of the plurality of ridges.

8. The suction swab according to claim 2, wherein the second end section of the resilient tip includes a sculpted surface that defines at least one ridge and at least two grooves.

9. The suction swab according to claim 8, wherein the second aperture is positioned on the at least one ridge.

10. The suction swab according to claim 8, further comprising: a bend portion formed in the intermediate portion of the suction tube, said bend portion being positioned closer to the first end portion than to the second end portion.

* * * * *